(12) United States Patent
Bond-Thorley et al.

(10) Patent No.: US 9,335,304 B2
(45) Date of Patent: May 10, 2016

(54) ULTRASONIC WHEEL SCANNER

(75) Inventors: Andrew Bond-Thorley, Stonehouse (GB); Richard Freemantle, Ashbourne (GB); Arthur O'Mahony, Manchester (GB); Luis Rivera, Mould (GB); Alun Williams, Holywell (GB); Andrew Philpot, Wrexham (GB); Neil Hankinson, Warrington (GB)

(73) Assignee: AIRBUS OPERATIONS LIMITED, Bristol (GB)

( * ) Notice: Subject to any disclaimer, the term of this patent is extended or adjusted under 35 U.S.C. 154(b) by 189 days.

(21) Appl. No.: 14/007,943

(22) PCT Filed: Mar. 22, 2012

(86) PCT No.: PCT/GB2012/050643
§ 371 (c)(1),
(2), (4) Date: Sep. 26, 2013

(87) PCT Pub. No.: WO2012/131334
PCT Pub. Date: Oct. 4, 2012

(65) Prior Publication Data
US 2014/0007689 A1 Jan. 9, 2014

(30) Foreign Application Priority Data
Mar. 28, 2011 (GB) .................................. 1105116.6

(51) Int. Cl.
*G01N 29/265* (2006.01)
*G01N 29/24* (2006.01)
*G01N 29/28* (2006.01)

(52) U.S. Cl.
CPC .......... *G01N 29/265* (2013.01); *G01N 29/2493* (2013.01); *G01N 29/28* (2013.01); *G01N 2291/106* (2013.01)

(58) Field of Classification Search
CPC ............ G01N 29/2493; G01N 29/265; G01N 2291/106; G01N 29/28
USPC ............................................................ 73/618
See application file for complete search history.

(56) References Cited

U.S. PATENT DOCUMENTS

| 3,148,535 | A | * | 9/1964 | Lemelson ........................ 73/600 |
| 3,205,702 | A |   | 9/1965 | Joy |
| 3,716,919 | A | * | 2/1973 | Evans, Jr. ......................... 33/781 |
| 4,185,501 | A | * | 1/1980 | Proudian et al. ................. 73/641 |
| 4,302,976 | A | * | 12/1981 | Bull ................................. 73/639 |
| 4,622,501 | A | * | 11/1986 | Eventoff et al. .............. 318/627 |
| 6,198,111 | B1 | * | 3/2001 | Donlon et al. ................ 250/584 |
| 6,571,636 | B1 | * | 6/2003 | McWhorter .................... 73/649 |

FOREIGN PATENT DOCUMENTS

| EP | 0023125 A1 | 1/1981 |
| EP | 1448983 B1 | 8/2004 |
| WO | 2009127854 A2 | 10/2009 |

OTHER PUBLICATIONS

British Search Report corresponding to GB 1105116.6, dated May 31, 2011.
International Search Report and Written Opinion corresponding to PCT/GB2012-050643, dated Jun. 28, 2012.

* cited by examiner

*Primary Examiner* — J M Saint Surin
(74) *Attorney, Agent, or Firm* — Hauptman Ham, LLP

(57) ABSTRACT

A scanner comprises a scanning array mounted within a rotatable assembly having a first wheel on a first side, a second wheel on a second side and a membrane forming a drum around the array wherein a load path is provided between the wheels to divert load from the membrane such that it can be made thinner.

7 Claims, 3 Drawing Sheets

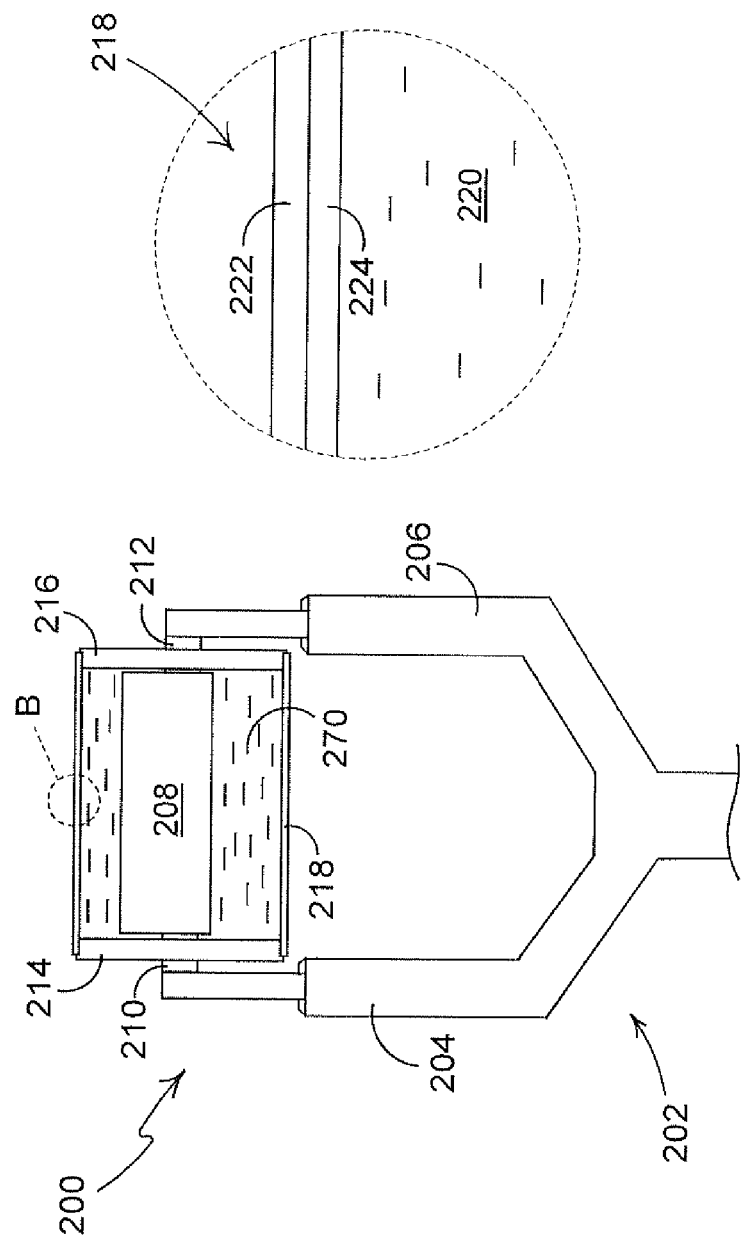

ULTRASONIC WHEEL SCANNER

RELATED APPLICATIONS

The present application is a National Phase of International Application Number PCT/GB2012/050643, filed Mar. 22, 2012, and claims priority from British Application Number 1105116.6, filed Mar. 28, 2011.

The present invention is concerned with an ultrasonic scanner. More specifically, the present invention is concerned with a wheel type ultrasonic scanner for non-destructive testing of composite engineering components, more particularly, aerospace components.

Due to the structure of composite components and, in particular, carbon fibre reinforced polymer components (CFRP), internal defects may occur during the manufacturing process or as a result of stresses in use. For example, delamination of the carbon layers may occur within the material which are invisible from the component exterior. Such defects may detrimentally affect the material properties to the extent that the component becomes weaker.

It is advantageous to be able to inspect the interior of composite components both following manufacture, and in testing or service.

Destructive testing will reveal the internal structure of the component (including any damage), however, the component is rendered useless. Although a sample of a manufactured batch may be destructively tested, this does not provide a 100% reliable indication that the entire batch is defect-free.

Therefore, non-destructive testing is extremely important with respect to composite components. Ultrasonic testing (UT) is a common technique in which sound waves are projected into the material and the reflected waves recorded and analysed.

Point to point testing in this manner is slow and laborious and, as such, various methods have been developed for "sweeping" a linear ultrasonic sensor array across the surface of a workpiece to provide a 2-D representation of a "slice" through the material. The intention is to maintain sonic coupling between the array and the workpiece. One coupling method utilises a rotatable, fluid-filled drum mounted around the ultrasonic array. The scanner is pushed along the surface of the material such that the drum rotates and maintains a constant coupling between the ultrasonic array and the workpiece. Such scanners are known as "wheel probes" or "wheel scanners". One such scanner is disclosed in EP1448983.

In general, wheel scanners are constructed having a central stationary axle to which the array is mounted. A wheel is mounted on each end of the central axle. The wheels are joined by a generally cylindrical thick membrane element which provides the contact surface for the workpiece. The two wheels and membrane form a "drum" which can be filled with a liquid couplant. Due to the existence of the thick membrane and its ability to transfer torque, the wheels rotate synchronously about the ultrasonic array, thus maintaining the scanner's orientation with respect to the workpiece. The membrane is also of sufficient thickness to ensure that the contact pressure between the drum and the workpiece is adequate to provide consistent coupling for the passage of ultrasonic waves.

The applicant of the present application has realised that beneficial effects can be achieved by reducing the thickness of the membrane. Providing a thinner membrane reduces the amount of attenuated acoustic energy and allows the user to scan further into the depth of the subject material such that thicker workpieces can be inspected.

A problem with making the membrane thinner is that is fails to satisfactorily provide a torsional load path between the two wheels. Uneven contact with the workpiece can thereby develop. Furthermore a fluid filled thin membrane delivers less contact pressure resulting in inconsistent coupling of ultrasonic waves.

It is an aim of the present invention to overcome, or at least mitigate, one or more of the above mentioned problems.

According to a first aspect of the invention there is provided an ultrasound scanner comprising: an ultrasound array defining a scanning vector, a coupling assembly having: a first member mounted at a first end of the array for rotation about a first axis, a second member mounted at a second, opposite end of the array for rotation about the first axis, and, a flexible coupling component extending between the first and second members to form a closed volume around the array, the coupling component having a workpiece contact surface intersected by the scanning vector, in which the first member and the second member are connected for synchronous rotation by a drive mechanism independent of the flexible coupling component.

By "drive path mechanism of the flexible coupling component" we mean there is provided a mechanism in which the load path between the members is independent—in other words a load path exists which does not pass through the flexible coupling component.

Advantageously, the provision of a drive path separate from the membrane mitigates or eliminates the requirement of the membrane to carry a torsional load between the wheels. As such, the membrane can be made much thinner because it no longer has to carry all of the torsional load between the wheels.

Preferably the drive mechanism is a geared drive linkage, preferably comprising a drive shaft rotatable about a second axis parallel to and offset from the first axis. Preferably the drive shaft is journalled in a bearing sleeve mounted fixed relative to the scanner.

Advantageously, the provision of a drive mechanism permits the positioning of the sensor array on the axis and allows for an off-centre mechanism to provide a functional link between the two wheels.

Preferably the drive shaft comprises a first gear formation engaged with a corresponding gear formation on the first member. More preferably the drive shaft comprises a second gear formation engaged with a corresponding gear formation on the second member.

Advantageously, by an appropriate transference of torque, e.g. by a geared arrangement, an offset shaft can carry the torsional load between the two wheels thus providing a separate load path from the membrane.

Preferably the member gear formations are ring gears defining radially inwardly facing gear teeth. Advantageously this permits easy assembly with the teeth of the internal shaft.

In order to further reduce the effects of any external forces on the membrane, a further coupling component may be provided extending between the members, the further coupling component being contracted from a stiffer material than the flexible coupling component. This is appropriate for axially longer scanners. The coupling components may be laminated.

According to a second aspect of the invention there is provided an ultrasound scanner comprising: an ultrasound array defining a scanning vector, a coupling assembly having: a first member mounted at a first end of the array for rotation about a first axis, a second member mounted at a second, opposite end of the array for rotation about the first axis, and, a flexible coupling component extending between the first and second members to form a closed volume around the array, the coupling component having a workpiece contact surface intersected by the scanning vector, in which the first member and the second member are connected for synchronous rotation by a drive path independent of the flexible coupling component.

By "drive path independent of the flexible coupling component" we mean the load path between the member is independent—in other words a load path exists which does not pass through the flexible coupling component. This does not preclude a member defining the drive path and the coupling component from being attached, or even laminated. Therefore, according to the invention the drive path may be defined by a further coupling component extending between the members, the further coupling component being contracted from a stiffer material than the flexible coupling component.

Preferably the further coupling component defines a closed volume around the array and is continued within the flexible coupling component. The further coupling component may be attached to the flexible coupling component, and may be a material layer laminated to an internal surface of the flexible coupling component.

By providing an alternative load path in this manner, a further coupling component constructed from a stiff material (therefore affording a thinner flexible member layer) can be used to transfer torque between the members. The material chosen can be significantly stiffer than the membrane and hence have a thickness affording little attenuation of sonic energy, whilst retaining a soft outer membrane which provides a good frictional contact with the workpiece.

The further coupling component may be constructed from a plastics material.

The flexible coupling component backed by a plastic layer (representing the further coupling component) may be used in conjunction with a mechanical drive mechanism. This allows the members to be synchronised (by the mechanism) whilst providing an extremely thin flexible coupling component, the shape an integrity of which is provided by the further coupling component.

Alternatively, or in addition, the closed volume may be filled with a pressurised fluid (above atmospheric pressure). The provision of a pressurised fluid (preferably a liquid offering good coupling characteristics such as water) exerts a radially outward force on the flexible coupling component and thereby helps it to hold its shape. Such force will also act to tighten the membrane in the axial direction which will improve torque transference between the members.

According to a third aspect of the invention, there is provided an ultrasound scanner comprising an ultrasound array defining a scanning direction, an ultrasound coupling component having a first member mounted for rotation about an axis at a first end of the array, a second member mounted for rotation about the axis at a second, opposite end of the array, and, a coupling component spanning the members and having a workpiece contact surface in the scanning direction, the coupling component comprising an outer material having a first stiffness and an inner layer having a second stiffness greater than the first.

Advantageously, the provision of a thin, stiff layer allows the membrane to be much thinner whilst maintaining the flexible outer material's contact abilities with the workpiece.

Preferably, the inner layer is a plastic coating which provides torsional rigidity without detrimentally affecting the acoustic properties of the component.

Pressurisation of a fluid (preferably a liquid) contained within a coupling component defining a closed volume will also aid the transference of torque between the members, the effect of which will aid the torque transference and stiffness provided by the inner layer.

Two example scanners, according to the present invention, will now be described with reference to the accompanying figures in which:

FIG. 3a is a side section view of a scanner in accordance with the second aspect of the invention; and FIG. 3b is a detail view of a part of the scanner of FIG. 3a.

Figure 1:
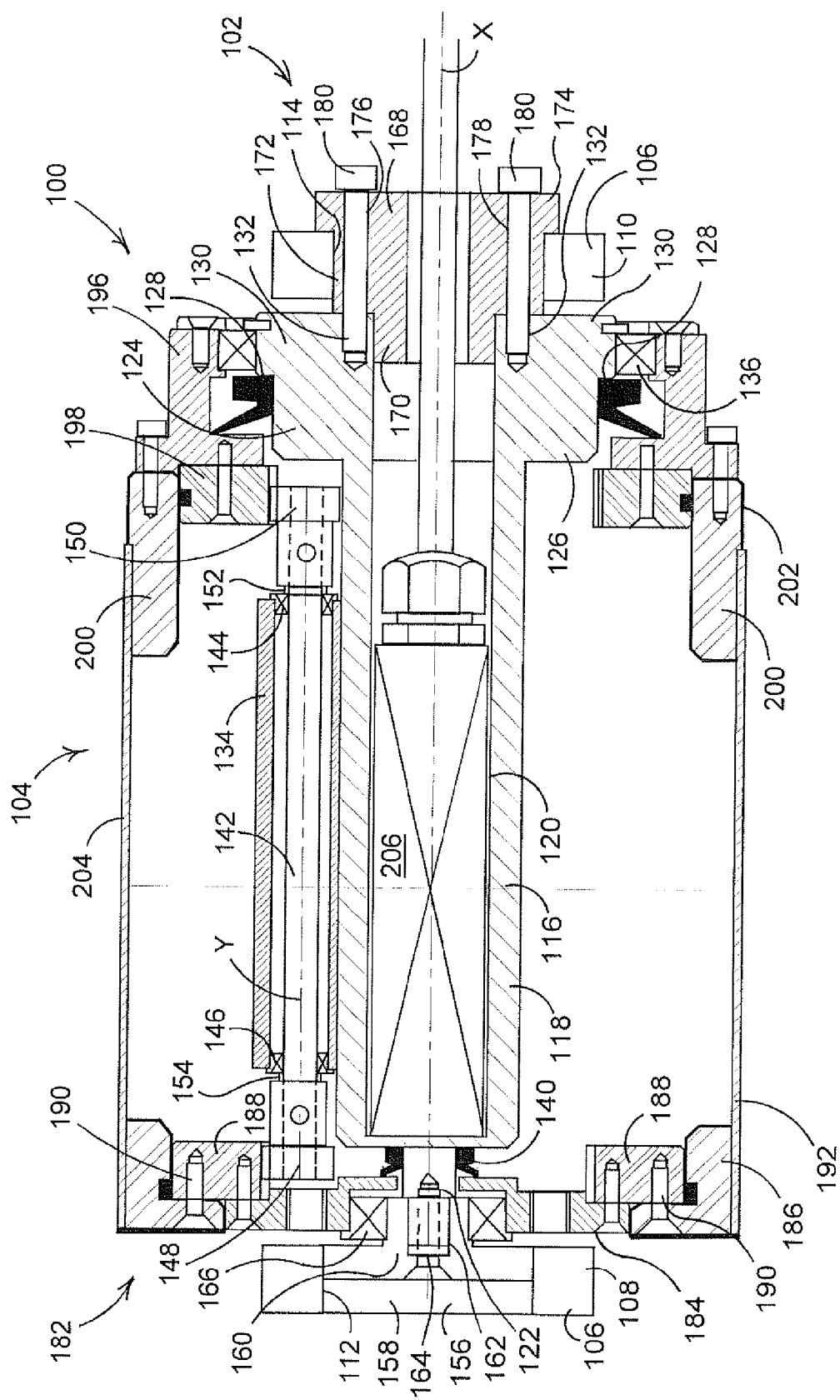
FIG. 1 is a plan section view of a scanner in accordance with a first aspect of the invention.
Figure 2:
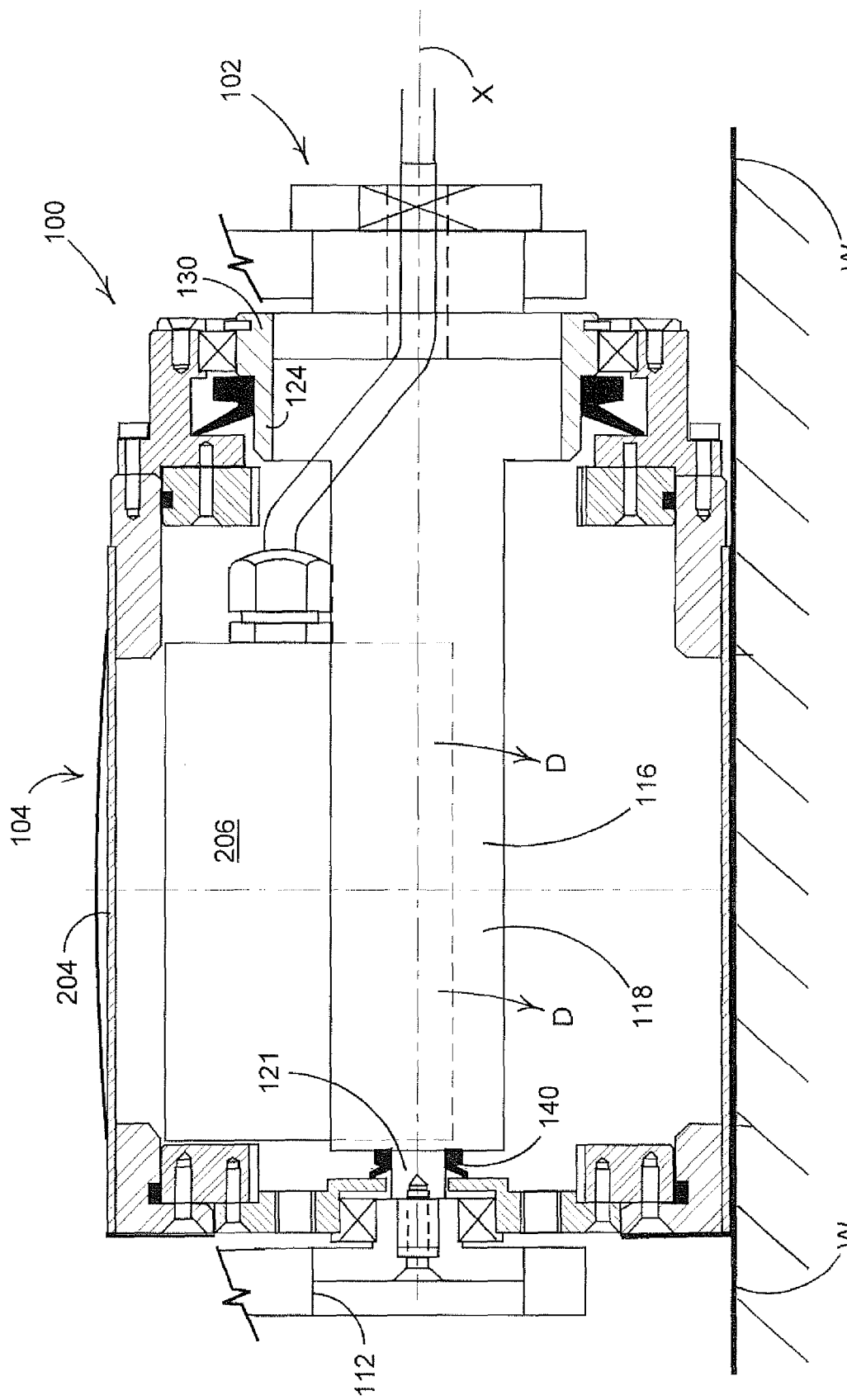
FIG. 2 is a side section view of the scanner of FIG. 1.

According to FIGS. 1 and 2, there is provided a scanner 100 having a chassis 102 and a rotatable assembly 104. The view is towards a workpiece being scanned (not shown).

The chassis 102 is non-rotatable and comprises a handle component 106 having a first side 108 and a second side 110. The sides 108, 110 are part of the same handle component 106 and meet at a position distant from the rotatable assembly 104 where a handle (not shown) is provided. As such, it will be understood that the first side 108 and the second side 110 are fixed non-rotatably with respect to each other. Each side 108, 110 defines a respective bore 112, 114 which bores are concentric about a first axis X.

The chassis 102 comprises a scanner mount 116 defining an elongate body 118 having a cavity 120 to receive a scanning array. A lug 121 is defined at a first end of the body 118, the lug 121 comprising an internally threaded axial bore 122. At a second opposite end of the body 118, a stepped annular collar 124 is defined having a first shoulder 126 proximate the elongate body 118 and a second shoulder 128 leading to an end collar region 130. The end collar region 130 defines two internally threaded bores 132.

A first roller bearing 136 is defined on an exterior cylindrical surface of the end collar region 130. A seal 138 extends from the collar 124 from the second shoulder 128.

At the opposite end of the elongate body 118, a further seal 140 surrounds the lug 120.

On a first side of the elongate body 118, a tubular sleeve 134 is affixed having a main axis Y parallel to, and offset from, the main axis X.

A drive shaft 142 is installed within the tubular sleeve 134 and is rotatably mounted by a pair of bearings 144, 146 at either end of the tubular member 134. The drive shaft 142 defines external gear formations 148, 150 at either end respectively. The gear formations are defined on gear members which are removably attached to the shaft in order to facilitate assembly with the tubular member 134. Circlips 152, 154 hold the shaft in place axially.

A first retaining member 156 is provided being a stepped annular component comprising a first section 158 sized for an interference fit with the bore 112 and which steps down to a second section 160 projecting towards the scanner mount 116. The second section 160 comprises an internally threaded bore 162. When assembled, a screw or bolt 164 couples the bores 122, 162 as shown in FIG. 1. A roller bearing 166 surrounds the second section 160 of the retaining member 156. It will be noted that the above described arrangement means that the scanner mount 116 is rigidly mounted to the first side 108 of the handle component 106.

Turning to the opposite end of the scanner mount 116, a second retaining member 168 is provided being a stepped annular component comprising a first section 170, dimensioned for an interference fit with the cavity 120 of the elongate body 118. A second section 172 is provided and has an interference fit with the bore 114 of the second side 110 of the handle component 106. A third section 174 abuts an exterior face of the second side 110 of the handle component 106. A pair of threaded bores 176, 178 are provided in the second retention member 168 parallel to the axis X which are aligned with the threaded bores 132 of the end collar region 130 of the scanner mount 116. Appropriate screws or bolts 180 are inserted to affix the second retaining member 168 to the scanner mount 116.

As such, it will be understood that the scanner mount 116 is secured from rotation relative to the handle component 106 by interference fits from the retaining members at both ends. Alternatively, non-circular shafts, keyways or splines may be used to prevent rotation of these components relative to the handle component 106.

Turning to the rotatable assembly 104, a first wheel 182 is provided having a hub part 184, a rim part 186 and an annular gear 188.

The rim part 186 is generally L-shaped and defines an outer cylindrical contact surface 192. The rim part 186 is fitted to the bearing 166 for rotation therewith. The rim part 186 encircles the hub part 184. The seal 140 abuts the hub part in sliding contact to maintain a fluid-tight seal therewith. The hub part 184 and the rim 186 are connected by affixing them both to an annular face of the ring gear 188 via bolts 190.

A second wheel 194 is also defined as part of the rotatable assembly 104 and comprises a hub part 196 which is engaged with the bearing 136 and rotatable therewith. The seal 124 contacts the hub pat 196 to form a fluid-tight seal therewith.

The hub part 196 is connected to both an annular gear 198 and a rim part 200, which is generally cylindrical presenting an outer contact surface 202.

A rubber membrane 204 spans the contact surfaces 192, 202 so as to define a cylindrical enclosure containing the scanner mount 116. The enclosure is filled with a couplant fluid, e.g. water which cannot escape due to seals 124, 140.

When assembled, the gear formation 148 engages the interior toothed surface of the annular gear 188 and the gear formation 150 engages the interior toothed surface of the annular gear 198. Because of this engagement, the rotation of the annular gears 188, 198 is linked. Any torque differential between the wheel assemblies 182, 194 is carried by a load path through the drive shaft 142. Therefore, regardless of the presence of the membrane 204, both of the wheels 182, 194 rotate at the same speed when driven.

In use, an ultrasonic transducer 206 is installed within the scanner mount 116 to project ultrasonic energy in a direction D perpendicular to axis X (see FIG. 2). The handle component 106 is held such that the direction D is towards a workpiece W and the ultrasonic energy passes through the membrane 204 to act on surface W. As the handle is pushed along parallel to the component W, friction between the membrane 204 and the surface of the workpiece W will cause the rotatable assembly 104 to rotate (actuating bearings 166, 136). Due to the drive shaft 142, no torsional load is carried by the membrane 204.

It will be noted that the rotation axis of the shaft Y is offset but parallel to the main axis X. It will also be noted that the shaft 142 is located to the side of the ultrasonic transducer 206 such that the scanning direction D does not pass through it. In the embodiment, the axis Y positioned 90 degrees away from the scanning vector D about main axis X.

Turning to FIGS. 3a and 3b, an alternative scanner 200 is shown comprising a handle 202 having a first side 204 and a second side 206 defining a fork-like formation. A scanning array 208 is disposed between the ends of the first and second sides 204, 206.

As with the scanner 100, the scanner 200 utilises a pair of axles 210, 212 each of which projects from the first and second sides of the handle 202 to meet the scanning array 208. A first wheel 214 is mounted on a first side 204 of the scanning array 208 and a second wheel 216 is mounted on a second side 206. A laminar membrane 218 extends between the wheels 214, 216 to form a cylindrical drum in which the scanning array 208 sits (surrounded by a couplant fluid 220). It will be noted that the wheels can be freely rotated but are constrained to each other by the laminar membrane 218. Turning to FIG. 3b, the membrane 218 is shown in more detail where it can be seen that it comprises an outer membrane 222 (constructed from a rubber material) and an inner plastic coating 224 constructed from a thin plastics material designed to provide some torsional stiffness between the wheels 214, 216.

It will be noted that the outer membrane 222 is sufficiently thin so as to provide the aforementioned benefits in terms of scanning a deeper thickness of workpiece. At the same time torsional rigidity is provided by a load path through the inner coating 224 which, although relatively rigid compared to the outer membrane 222, is sufficiently thin so as not too significantly detriment the ability of the scanning array 208 to scan the workpiece.

The laminar membrane, therefore, combines the high friction properties of rubber with the stiffness of a plastics material.

The invention claimed is:

1. An ultrasound scanner comprising:
   an ultrasound array defining a scanning vector,
   a coupling assembly having:
      a first member mounted at a first end of the array for rotation about a first axis,
      a second member mounted at a second, opposite end of the array for rotation about the first axis, and,
      a flexible coupling component extending between the first and second members to form a closed volume around the array, the coupling component having a workpiece contact surface intersected by the scanning vector,
   wherein the drive mechanism comprises a drive shaft rotatable about a second axis parallel to and offset from the first axis about which the first member and the second member are connected for synchronous rotation by a drive mechanism independent of the flexible coupling component.

2. An ultrasound scanner according to claim 1 in which the drive shaft is journalled in a bearing sleeve mounted fixed relative to the scanner.

3. An ultrasound scanner according to claim 2 in which the drive shaft comprises a first gear formation engaged with a corresponding gear formation on the first member.

4. An ultrasound scanner according to claim 3 in which the drive shaft comprises a second gear formation engaged with a corresponding gear formation on the second member.

5. An ultrasound scanner according to claim 4 in which the member gear formations are ring gears defining radially inwardly facing gear teeth.

6. An ultrasound scanner according to claim 1 in which the closed volume contains a pressurised fluid.

7. An ultrasound scanner according to claim 6 in which the pressurised fluid is a liquid.

* * * * *